United States Patent [19]

Taylor

[11] Patent Number: 5,036,009
[45] Date of Patent: * Jul. 30, 1991

[54] BIOCHEMICAL PROCESS

[75] Inventor: Stephen C. Taylor, Clwyd, Wales

[73] Assignee: Imperial Chemical Industries PLC, London, England

[*] Notice: The portion of the term of this patent subsequent to Apr. 2, 2002 has been disclaimed.

[21] Appl. No.: 687,935

[22] Filed: Dec. 31, 1984

Related U.S. Application Data

[62] Division of Ser. No. 433,093, Oct. 6, 1982.

[30] Foreign Application Priority Data

Oct. 6, 1981 [GB] United Kingdom ............... 8130116

[51] Int. Cl.$^5$ .................. C12N 1/20; C12N 1/26; C12N 15/00; C12P 1/26
[52] U.S. Cl. ................... 435/253.3; 435/155; 435/156; 435/248; 435/172.1; 435/877
[58] Field of Search ............ 435/155, 156, 248, 253, 435/172.1, 877

[56] References Cited

U.S. PATENT DOCUMENTS 3,326,770  6/1967  Coty ................................. 435/877
4,259,444  3/1981  Chakrabarty ..................... 435/253

OTHER PUBLICATIONS

DeFrank, J. J. et al., "The P-Cymene Pathway in *Pseudomonas putida* PL: Isolation of a Dihydrodiol Accumulated by a Mutant", *Biochem and Biophys. Res. Common.*, vol. 70, No. 4 (1976), pp. 1129–1135.
American Type Culture Collection, *Catalogue of Strains I*, 15th Edition (1982) p. 177.
*Chemical Abstracts*, vol. 80, No. 21, p. 202, Abstract No. 117992t, "Microbial Degradation of Automatic Hydrocarbons".
*Chemical Abstracts*, vol. 79, No. 5, p. 90, Abstract No. 27793d, "Initial Reactions in the Oxidation of Ethylbenzene by *Pseudomonas putida*".
*Chemical Abstracts*, vol. 81, No. 23, p. 226, Abstract No. 148261d, "Bacterial Metabolism of Para-and Meta-Xylene Oxidation of the Aromatic Ring".
*Chemical Abstracts*, vol. 73, No. 1, p. 92, Abstract No. 1091z, "Oxidative Degradation of Aromatic Hydrocarbons by Microorganisms. Formation of (+)-cis-2,-3-Dihydroxy-1-Methyl-4,6-Cyclohexadiene from Toluene by *Pseudomonas putida*".
*Chemical Abstracts*, vol. 75, No. 25, p. 88, Abstract No. 148792d, "Metabolism of Biphenyl by *Pseudomonas putida*".
*Chemical Abstracts*, vol. 88, No. 21, p. 542, Abstract No. 151886m, "The Absolute Stereochemistry of Several Cis-Dihydrodiols Microbially Produced from Substituted Benzenes".
*Chemical Abstracts*, vol. 70, No. 3, p. 71, Abstract No. 9463f, "Oxidative Degradation of Aromatic Hydrocarbons by Microorganisms II. Metabolism of Halogenated Aromatic Hydrocarbons".
Jerina, D. M. et al., *Journal of the Amer. Chem. Soc.*, vol. 92, No. 4, pp. 1056–1059 (1970), "The Role of the Arene Oxide-Oxepin System in the Metabolism of Aromatic Substrate. IV Stereochemical Considerations of Dihydrodiol Formation and Dehydrogenation".
Jerina, D. H. et al., *Jour. of the Amer. Chem. Soc.*, vol. 98, No. 19, pp. 5988–5996(1976), "Dihydrodiols from Anthracene and Phenanthrene".
Reineke, W. et al., *Tetrahedron*, vol. 34, pp. 1707–1714(1978), "Cis-Dihydrodiols Microbially Produced from Halo-and Methylbenzoic Acids".
Gibson et al., Biochemistry, vol. 9, No. 7, pp. 1631–1635 (1970), "Incorporation of Oxygen-18 into Benzene by *Pseudomonas Putida*". (1973).
Gibson et al., Biochemistry, vol. 12, No. 8, pp. 1520–1528, "Initial Reactions in the Oxidation of Ethylbenzene by *Pseudomonas putida*".
Gibson et al., *Biochemistry*, vol. 9, No. 7, pp. 1626–1630, (1970), "Formation of (+)-Cis-2,3-Dihydroxy-1-Methylcyclohexa-4,6-Diene from Toluene by *Pseudomonas putida*".
Gibson et al., Biochemistry, vol. 7, No. 7, pp. 2653–2662 (1968), "Oxidative Degradation of Aromatic Hydrocarbons by Microorganisms. I. Enzymatic Formation of Catechol From Benzene".
Daly, J. W. et al., Arch. Biochem. Biophys., vol. 142, pp. 394–396 (1971), Cis-1,2-Dihydroxy-1,2-Dihydronaphthalene: A Bacterial Metabolite from Naphthalene.
De Frank, J. J. et al., *Jour. of Bacteriol.*, vol. 129, No. 3, pp. 1356–1364 (1977), "p-Cymene Pathway in *Pseudomonas Putida*: Initial Reactions".
Walker, N. et al., J. Gen. Microbiol, vol. 8, pp. 273–276 (1955), "The Breakdown of Napthalene by a Soil Bacterium".
Berget's Manual of Determinative Bacteriology (8th Ed). (Buchanan & Gibbons, eds.), Williams & Wilkins Co., Baltimore, Md., p. 222, 1974.

*Primary Examiner*—Elizabeth C. Weimar
*Assistant Examiner*—Gail Poulos
*Attorney, Agent, or Firm*—Cushman, Darby & Cushman

[57] ABSTRACT

The production of 1,2-dihydroxy-cyclohexadienes from aromatic compounds by a biochemical process by using strains of *Pseudomonas putida*, and novel 1,2-disubstituted-cyclo-hexadienes are described. Certain of the novel compounds are useful as intermediates in the production of polymers.

1 Claim, No Drawings

BIOCHEMICAL PROCESS

This is a division, of application Ser. No. 433,093, filed Oct. 6, 1982.

This invention relates to the production of cyclic dihydroxy compounds by a biochemical process, and to certain novel cyclic dihydroxy compounds.

The production of cyclic dihydroxy compounds by supplying aromatic compounds to mutant strains of Pseudomonas species, Alkaligenes species and Beirjerinckia species, which in their natural form can utilise certain aromatic compounds as carbon sources for growth, is known. The concentrations of cyclic dihydroxy compounds produced by such microorganisms are low, typically less than 2 grams per liter of fermenting liquor. Additionally, the enzymes for the production of cyclic dihydroxy compounds have to be induced in the cells before their use, by exposure thereof to aromatic compounds.

We have now found that when cells of certain mutant strains of *Pseudomonas putida* are fed with aromatic compounds higher concentrations of cyclic dihydroxy compounds than hitherto achieved are obtained, and that a wider range of aromatic compounds can be converted into cyclic dihydroxy compounds. The cyclic dihydroxy compounds produced by the aforesaid mutants are useful intermediates in the production of ring-containing polymers as is more fully described in our copending United Kingdom Patent Application No. 8130114.

Representative cultures of *Psuedomonas putida* which are suitable for mutation to form the mutant strains useful in the present invention have been deposited with the National Collection of Industrial Bacteria, Torrey Research Station, Aberdeen, Scotland, UK where they have been assigned the numerical designation NCIB 11680 and NCIB 11767.

We have prepared first mutant strains of *Pseudomonas putida* NCIB 11680 and *Pseudomonas putida* NCIB 11767 which are no longer able to grow on benzene or toluene and which produce cyclic dihydroxy compounds from certain aromatic compounds. We have also produced from the first mutant strain of *Pseudomonas putida* NCIB 11767 further mutant strains which are constitutive for an enzyme that converts certain aromatic compounds into cyclic dihydroxy compounds (hereinafter referred to for convenience as "constitutive strain"). The constitutive strain affords the advantage that an enzyme induction step is not needed before production of cyclic dihydroxy compounds by the microorganism can occur.

Accordingly, the present invention provides a process for the preparation of cyclic dihydroxy compounds which process comprises supplying a suitable aromatic or substituted aromatic compound and a suitable energy source to a suitable mutant strain of *Psuedomonas putida* in a medium which supports little and preferably substantially no growth of the cells of the mutant strain.

Whilst the aromatic compound used in the process of the present invention is preferably monocyclic we do not exclude the possibility that it may comprise a plurality of cyclic rings, e.g. naphthalene, and biphenyl, Where a substituted aromatic compound is used in the process of the present invention it may have one or more substituents, which substituents may be hydrocarbyl groups, having one to four carbon atoms, e.g. methyl, ethyl or vinyl and/or heteroatoms or heterogroups, e.g. halogen.

The aforementioned first mutant strains of *Pseudomonas putida* which may be used in the process of the invention, and in which an enzyme which converts aromatic compounds into cyclic dihydroxy compounds is inducible, may be prepared by treating *Pseudomonas putida* NCIB 11680 or preferably *Pseudomonas putida* NCIB 11767 under mutating conditions therefore to give mutant strains which are no longer capable of utilising toluene or benzene as a sole source of carbon for growth and which when grown, in a liquid medium containing pyruvic acid as a carbon source, in the presence of toluene, excrete a substance which has a UV absorbance peak at 265 nanometers. The aforesaid mutation may be effected by chemical and/or physical means. Chemical mutation may be effected for example by treatment of the microorganism with N-methyl-N'-nitro-N-nitrosoguanidine, which treatment can be conveniently effected as described by Ornston, Journal of Biological Chemistry, 1966, Volume 241, pages 3800–3810. Physical mutation may be effected by electromagnetic radiation, e.g. UV light.

The aforementioned constitutive strain which may be used in the process of the present invention may be prepared by treating the first mutant strain of *Pseudomonas putida* NCIB 11767 under mutating conditions as hereinbefore described to give strains which after growth in the absence of an aromatic compound, have the ability to produce cyclic dihydroxy compounds from aromatic compounds. Choice of suitable constitutive strains from the product of the mutation treatment may be facilitated by growing the cells after mutation on a solid agar medium containing pyruvic acid or glucose as carbon source. After growth, the colonies on the agar plates may be sprayed with a solution of catechol in water, colonies of cells which rapidly turn yellow/green are constitutive for an enzyme which converts catechol into 2-hydroxymuconic semialdehyde (Nozaki, Topics in Current Chemistry (English Review) 1979, Volume 78, pages 145–186). This enzyme catalyses one of the steps in the oxidative degradation of benzene in *Pseudomonas putida* NCIB 11680 and *Pseudomonas putida* NCIB 11767 and we have found that it is linked in its expression to the enzyme which converts benzene to the cyclic dihydroxy compound. Therefore those cells which turn green on exposure to catechol are the desired constitutive strain.

The constitutive strain may be susceptible to catabolite repression by carbon sources such as glucose and casamino acids. Improved constitutive strains which are not susceptible to such catabolite repression may be obtained by mutation of the constitutive strains, by treatments as hereinbefore described. The improved constitutive strains can be detected by growing colonies of the constitutive strains which have been subjected to a mutation treatment on an agar medium which contains a mixture of glucose and casamino acids as carbon sources, the colonies which turn yellow/green on exposure to catechol comprise the improved constitutive strain.

Cells of the mutant strains for use in the process of the present invention may be grown in conventional growth media as a continuous, batch or fed-batch technique. Where the first mutant strains are used in the process of the present invention they are preferably grown by a fed-batch technique in which an aromatic compound is supplied to the culture whilst feeding fresh medium thereto.

The growth medium in which mutant strains for use in the present invention may be grown comprises an aqueous mineral salts solution and a suitable carbon source. The carbon source may be, for example, acetic acid, glucose or ethanol. The concentration of carbon source can vary over a wide range but is generally between 1% (w/v) and 5% (w/v). Oxygen or an oxygen containing gas, must be present during the growth period. The temperature of the medium during the growth period may vary considerably but normally will be in the range of 25° C. to 35° C. The pH of the medium is kept within the range of 5.5 to 8.0 during growth and preferably at 6.5 to 7.5. The size of the culture can vary considerably for example between 1.5 and 500 liters.

Following the growth period the cells are used in the process of the present invention. The cells may be harvested, for example by centrifugation or flocculation, or they may be used directly in the process of the present invention. Where the cells are harvested they are resuspended in a mineral salts solution which does not support significant cell growth, e.g. phosphate or tris(hydroxymethyl)aminomethane buffer solutions or conventional growth medium but which lacks or contains little of one or more essential elements. Typically the concentration of resuspended cells is 1 to 30 grams dry weight per liter. The cells are kept at a temperature of 20° C. to 40° C. and the pH maintained between 7.5 and 8.5. Oxygen or an oxygen containing gas is added to the cell suspension such that the oxygen tension is kept at greater than 1% of saturation. A suitable energy source is supplied, preferably as a continuous feed, to the cell suspension such that the concentration of the energy source is maintained at a suitable concentration, preferably between 0.05% (w/v) and 0.5% (w/v). Examples of suitable energy sources include inter alia, alcohols e.g. ethanol, carboxylic acids, e.g. acetic acid, and carbohydrates e.g. glucose. Preferably the energy source is ethanol or acetic acid.

The aromatic hydrocarbon, e.g. benzene, chlorobenzene, toluene, may be added to the cell suspension as a vapour in the stream of oxygen or oxygen-containing gas but preferably, where it is a liquid, is added as a liquid.

The rate of addition of the aromatic hydrocarbon to the culture of a mutant strain in the process of the present invention is typically about 0.5 to 10 grams per gram dry weight of cells per hour. The rate of addition of the energy source may vary during the conversion but is typically in the range 0.1 to 2.0 grams per gram dry weight of cells per hour. The productive lifetime of the cell suspension is typically between 5 and 50 hours. After this period the cells are removed by centrifugation and/or flocculation. Fresh cells may be added to the supernatant liquor and the process repeated. At the end of the process the supernatant liquor typically contains between 10 and 50 grams per liter of a cis-1,2-dihydroxy-cyclohexa-3,5-diene or a homologue or analogue thereof.

The cyclic dihydroxy products of the process of the present invention are preferably extracted from the aqueous reaction mixture by solvent extraction with a suitable polar solvent. Examples of polar solvents which may be used include inter alia ethyl acetate, diethyl ether and methylene chloride. More preferably continuous extraction procedures are employed. However, we do not exclude the possibility that, for example, the aqueous medium, after separation of the cells, is evaporated and the residue dissolved in a suitable solvent, e.g. methanol, ethanol or methylene chloride.

A further aspect of the present invention provides compounds of the general formula:

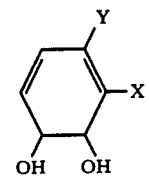

wherein X and Y, which may be the same or different, represent hydrogen, halogen, aryl, e.g. phenyl, or cyano groups except that X and Y both cannot be hydrogen.

Preferably Y is hydrogen, X is chloro, bromo or fluoro; and the hydroxy groups are cis to each other.

The dihydroxy compounds prepared by the process of the present invention may be converted into derivatives thereof, e.g. acetate, benzoate, pivalate, carbonate, which derivatives may often be converted into polymers and copolymers thereof as is more fully described in our copending United Kingdom Patent Application No. 8130114.

Various aspects of the present invention will now be described by reference to the following Examples which are illustrative of the invention.

GROWTH MEDIA

Medium A

Concentrated phosphoric acid (0.7 g/liter), $MgSO_4.7H_2O$ (1.6 g/liter), $K_2HPO_4.3H_2O$ (0.9 g/liter), ammonium sulphate (1.5 g/liter), ferrous sulphate (0.025 g/liter), $CuSO_4.5H_2O$ (0.001 g/liter), $MnSO_4.4H_2O$ (0.005 g/liter), $ZnSO_4.7H_2O$ (0.005 g/liter) and calcium carbonate (0.065 g/liter); the pH was adjusted to 7 with sodium hydroxide.

Medium B

Medium A containing 1% w/v pyruvic acid and 0.5% w/v acetic acid.

Medium C

Medium A lacking the ammonium sulphate.

Medium D

Medium A containing 1% w/v pyruvic acid.

Medium E

Concentrated phosphoric acid (2.2 grams/liter), $MgSO_4.7H_2O$ (0.8 grams/liter), $K_2SO_4$ (0.45 grams/liter), $(NH_4)_2SO_4$ (5 grams/liter), $FeSO_4.7H_2O$ (0.04 grams/liter), $CuSO_4.5H_2O$ (1 mg/liter), $MnSO_4.4H_2O$ (5 mg/liter), $CaCO_3$ (65 mg/liter), and glucose (15 grams/liter); the pH was adjusted to 7.5 with sodium hydroxide solution.

Medium F

Bauschop and Elsdon's medium as described in Journal of General Microbiology, 1960, Volume 23, pages 457–469.

Medium G

Luria liquid medium as described in "Experiments in Molecular Genetics" by J. H. Miller, published by Cold Spring Harbor Laboratories, New York, 1972.

PREPARATION OF A MUTANT STRAIN OF PSEUDOMONAS PUTIDA NCIB FOR USE IN THE PRESENT INVENTION

Pseudomonas putida NCIB 11680 was grown to early exponential growth in a mineral salts medium containing 0.2% w/v sodium acetate as carbon source. The cells were harvested by centrifugation and resuspended at a concentration of 0.2 grams dry cell weight per liter in 20 ml of 25 millimolar citric acid-sodium citrate buffer at pH 5.5 containing 1 mg of N-methyl-N'-nitro-N-nitrosoguanidine. The suspension was incubated for 40 minutes at 30° C. after which the cells were harvested by centrifugation and washed three times with 25 millimolar citrate buffer at pH 5.5. The cells were grown overnight in 0.2% (w/v) sodium acetate mineral salts medium, and after serial dilution, were plated on 0.4 millimolar sodium acetate mineral salts agar. The plates (100) were incubated in paint tins (capacity 2.5 liters) each of which contained a vial holding 10 ml of 10% (w/v) toluene in water. After 3 days incubation at 30° C., 30 prospective mutants, i.e. colonies of diameter less than 0.5 mm, were picked off and regrown on a 0.2% (w/v) sodium pyruvate mineral salts agar.

Each mutant was grown in a 250 ml Erlenmeyer flask, shaken in a water bath at 30° C., containing 50 ml of 0.2% (w/v) sodium pyruvate mineral salts solution with toluene provided in the gas phase as in the procedure described by Gibson, Hensley, Yoshioka, and Mabry, in Biochemistry, 1970, Volume 9, pages 1626–1630. After 20 hours growth, 1 ml samples were centrifuged and the UV spectrum of the clear supernatants were examined between 300 and 220 nanometers. Two mutants produced supernatant liquids containing a compound with a maximum absorbance at 265 nanometers of 72 and 65 respectively. The mutant which had the absorbance maximum of 72 is hereinafter referred to for convenience as mutant strain A.

PREPARATION OF MUTANT STRAINS OF PSEUDOMONAS PUTIDA NCIB 11767 FOR USE IN THE PRESENT INVENTION

Pseudomonas putida NCIB 11767 was grown to early exponential phase in Medium G. The cells were harvested by centrifugation and resuspended at a concentration of 0.2 grams dry cell weight per liter in 20 ml of 25 millimolar citric acid-sodium citrate buffer, pH 5.5 containing 1 mg of N-methyl-N'-nitro-N-nitro-soguanidine (NTG). After 45 minutes at 30° C. the cells were harvested by centrifugation, washed twice with medium F and then grown overnight in medium F containing 0.3% (w/v) sodium pyruvate at 30° C. After serial dilution, cells were plated on a medium F agar containing 0.3 millimolar sodium pyruvate and incubated in 1 liter paint tins each containing 0.5 ml benzene in a vial. After 3 days at 30° C. 144 prospective mutants, i.e. colonies less than 0.5 mm diameter, were picked off and regrown on a 0.2% w/v sodium pyruvate, medium F agar.

90 of these mutants were screened for the production from benzene of a compound absorbing at 260 nanometers as hereinbefore described. One mutant which gave a supernatant liquid with a maximum absorbance at 260 nanometers of 37 is hereinafter referred to for convenience as mutant strain B.

PREPARATION OF CONSTITUTIVE STRAINS FROM MUTANT B

The procedure used for mutagenisis was as hereinbefore described. After treatment with NTG, the washed, diluted cells were plated onto medium F agar plus 10 millimolar sodium pyruvate. After two days at 30° C., colonies were sprayed with a solution of catechol in water (0.5 molar) and those which turned yellow/green after 5 minutes were selected. From a total of $1.8 \times 10^5$ colonies screened, 35 yellow/green colonies were selected. Each of these was grown overnight in 16 ml of medium F plus 0.3% (w/v) sodium pyruvate. Cells were harvested and resuspended in 10 ml of 25 mM potassium phosphate buffer, pH 7.8, containing 0.4%0.4% (v/v) ethanol. These cultures, in 250 ml conical flasks, were incubated overnight, each in the presence of 0.5 ml toluene as hereinbefore described. Supernatants were examined after this time for compounds absorbing at 265 nanometers. A constitutive mutant which gave an absorbance at 265 nanometers of 250 was selected and is hereinafter referred to for convenience as mutant strain C.

Mutant strain C was grown at 30° C. in 20 ml of medium G to early exponential phase and after harvesting, cells were resuspended in 40 ml of 0.1 molar $MgSO_4.7H_2O$. A 5 ml aliquot was UV-irradiated in a glass petri dish for 45 seconds at a dose of 1.6 $\mu W/cm^2 \times 100$. The cells were then grown in the dark in five 20 ml aliquots of medium F plus 10 millimolar sodium pyruvate.

After 2 days at 30° C. cultures were serially diluted and plated onto medium F plus 75 millimolar glucose and 1% (w/v) vitamin free casamino acids (ex Difco Inc., Detroit, Mich., U.S.A.) and incubated for a further 2 days at 30° C. Colonies were then sprayed with catechol as hereinbefore described and yellow/green colonies were selected. From a total of $4 \times 10^4$ colonies screened, 10 were selected and grown overnight in 10 ml of medium F plus 75 millimolar glucose and 1% (w/v) casamino acids at 30° C. Cells were harvested and resuspended as above in phosphate buffer plus ethanol and irradiated at 70° C. in the presence of 0.5 ml toluene as hereinbefore described. A constitutive mutant, less affected then mutant C by catabolite repression was selected which gave an absorbance at 265 nanometers of 61.2. (Mutant strain C under identical conditions produced an absorbance of 15.6). This mutant is hereinafter referred to for convenience as mutant strain D.

EXAMPLE 1

This example illustrates the preparation of cis-1,2-dihydroxycyclohexa-3,5-diene by the process of the present invention.

40 liters of medium B were inoculated, in a stirred fermenter, with the mutant strain A to give an initial cell density of approximately 0.2 grams cell dry weight per liter of the medium. After 8 hours growth, a further portion of medium B was added to the culture at a rate of 2 liters per hour for 4 hours. Then toluene, at a rate of addition of 16.5 grams per hour, was added to the culture for 10.5 hours. The cells were then harvested at a cell density of 5.5 grams cell dry weight per liter.

A portion of the cells were resuspended in 5.0 liters of medium C to give a cell density of 25 grams cell dry weight per liter. Ethanol was continuously added to the cell suspension at a rate of 6 grams per hour. Benzene was added to the cell suspension as a vapour in the air stream at a rate of 20 grams per hour. The temperature was maintained at 30° C. and pH was maintained at 7.5. Air was added to the stirred cell suspension at a rate of 1.5 liters per minute. After 18 hours the experiment was terminated when the concentration of cis-1,2-dihydroxy-cyclohexa-3,5-diene in the supernatant solution was 13 grams per liter.

The supernatant solution was concentrated by rotary evaporation at 60° C. to a volume of 1 liter. The cyclic dihydroxy compound was continuously extracted with 500 ml methylene chloride for 24 hours. The methylene chloride solution was concentrated by rotary evaporation at 30° C.; addition of pentane to the concentrate gave crystals (30 grams) which were shown by melting point, n.m.r., mass spectroscopy and u.v to be cis-1,2-dihydroxycyclohexa-3,5-diene.

EXAMPLE 2

The procedure of Example 1 was repeated except that after the cells had been resuspended in medium C ethanol was added thereto to a concentration of 0.3% w/v; and benzene and ethanol were added as a mixture (70:30), instead of separately, at a rate of 23 grams of mixture per hour.

EXAMPLE 3

This example illustrates the preparation of cis-1,2-dihydroxy-3-chloro-cyclo-hexa-3,5-diene by the process of the present invention.

Mutant strain A was grown as a batch culture in medium A with 1% (w/v) pyruvic acid as carbon source. At a cell density of 1 gram cell dry weight per liter (after 4 hours growth), toluene was added to the culture in the air stream (toluene addition rate of 3 grams per hour) and the fermentation was continued for a further 16 hours. Cells were harvested at a dry weight of 1.5 grams per liter.

Cells were resuspended in 3.0 liters of Medium C to give a cell density of 10 grams cell dry weight per liter. Ethanol (15 gram) was added to the cell suspension. Chlorobenzene was added to the cell suspension as a vapour in the air stream (1.2 liters per minute) at a rate of 4 grams per hour. The pH of the suspension was maintained at 7.5 and the temperature of the suspension was maintained at 30° C. After 24 hours the cells were removed and the reaction mixture was concentrated by rotary evaporation at 60° C. under reduced pressure to a volume of approximately 400 ml. The concentrate was continuously extracted with ether (250 ml) for 16 hours then the ether solution was dried over anhydrous $MgSO_4$. Evaporation of the solvent from a filtered aliquot (50 ml) of this solution gave a crude solid (1.92 g) which was recrystallised from toluene/pentane to give cis-1,2-dihydroxy-3-chlorocyclohexa-3,5-diene as colourless crystals (1.70 g) m.p. 95°–96° C.; proton magnetic resonance spectrum (100 MHz) in deuterochloroform at 29° C. gave signals at $\delta 2.5$(2H, singlet, disappears on shaking the solution with $D_2O$), $\delta 4.2$(1H, $J_{1,2}6.4$ Hz, $J_{1,6}11.4$ Hz, H-1), $\delta 4.5$(1H, doublet, $J_{2,1}6.4$ Hz, H-2), $\delta 5.8-6.2$(3H, multiplet, H-4, H-5 and H-6); infra-red spectrum (KBr disc) had peaks at 3280, 1640, 1580, 1380, 1340, 1310, 1280, 1170, 1090, 1040, 1000, 990, 930, 880, 835, 795, 670, 590 and 390 $cm^{-1}$.

EXAMPLE 4

This example illustrates the preparation of cis-1,2-dihydroxy-3-methyl-cyclohexa-3,5-diene by the process of the present invention.

The procedure of Example 3 was repeated except that toluene was used instead of chlorobenzene.

The concentration of cis-1,2-dihydroxy-3-methyl-cyclohexa-3,5-diene in the fermenting liquid was 16 grams per liter. It was extracted continuously with diethyl ether. Addition of pentane to the ether solution gave crystals (28 grams) which were shown by melting point, n.m.r., i.r. and mass spectroscopy to be cis-1,2-dihydroxy-3-methylcyclohexa-3,5-diene.

EXAMPLE 5

This example illustrates the use of a constitutive mutant in the process of the present invention.

Mutant strain D was inoculated into 20 liters of medium E to give an initial cell density of 0.2 grams dry weight of cells/liter. Temperature was maintained at 30° C. and pH at 7.2. The fermenter was stirred at 500 r.p.m. and air was added at a rate of 6 liters/minute. After 16 hours the cells were harvested by centrifugation at a cell density of 4 grams cell dry weight/liter.

A portion of the cells was resuspended in 3 liters of 25 mM potassium phosphate buffer, pH 7.6 containing 1 gram of $FeSO_4.7H_2O$ and 12 ml of ethanol. The cell density was 9 gram dry weight/liter. Temperature was kept at 30° C. and pH at 7.6 with sodium hydroxide solution. An air/oxygen mixture was added (1.0 liters/minute) to give an oxygen tension of 10% saturation. The reactor was stirred at 1400 r.p.m. Benzene was added as a liquid to the reactor at a rate of 20 grams/hour and a further 18 mls of ethanol were added in three aliquots at 2 hour intervals. After 7 hours, the cells were removed by centrifugation to leave 3 liters of supernatant containing 29 grams/liter of cis-1,2-dihydroxycyclohexa-3,5-diene.

EXAMPLE 6

This example illustrates the use of a constitutive mutant to produce high concentrations of cis-1,2-dihydroxycyclohexa-3,5-diene by the process of the present invention.

Mutant strain C was grown for 16 hours as a 20 liter batch culture at 30° C., pH 7.0 in medium D. The cells were harvested at a dry weight of 3 gram per liter, and resuspended in 5 liters of 25 mM potassium phosphate buffer pH 7.8 containing 0.5 g $FeSO_4$ $7H_2O$. Air was added at a rate of 1 liter per minute, the reaction mixture was stirred at 800 r.p.m. and the temperature was maintained at 30° C. Benzene was added as a vapour in the air stream at a rate of 20 grams per hour for 20 hours and a total of 40 grams of ethanol was added as for aliquots. After 20 hours the supernatant liquid contained a total of 123 grams of cis 1,2-dihydroxycyclohexa-3,5-diene at a concentration of 24.6 grams per liter.

EXAMPLE 7

Mutant strain D was grown for 16 hours as a 20 liter batch culture in medium E at 30° C., pH 7.0. After harvesting a portion of the cells was resuspended in 4 liters of the medium described in Example 6 to a cell density of 5 grams dry weight per liter. Benzene, as a liquid, (12 grams per hour) and a continuous ethanol feed (2.5 grams per hour) were added to the culture.

After 8 hours the cells were removed to leave a supernatant fluid containing cis-1,2-dihydroxycyclohexa-3,5-diene at a concentration, based on the known extinction coefficient for this compound (Nakajima et al Chemische Berichte, 1959, Volume 92, page 163), of 15 grams per liter.

To the supernatant fluid a further portion of cells was added to a cell density of 8 grams cell by weight per liter and the experiment continued. After a further 16 hours, the supernatant fluid contained cis 1,2-dihydroxycyclohexa-3,5-diene at a concentration of 40 grams per liter.

EXAMPLE 8

The procedure of Example 6 was repeated except that naphthalene was used instead of benzene. The naphthalene was added at the start of the experiment to give a concentration of 1.5% w/v.cis-1,2-dihydroxy-1,2-dihydronaphthalene was obtained (20 grams).

EXAMPLES 9-11

The procedure of Example 7 was repeated except that fluorobenzene, benzyl alcohol and biphenyl were separately used instead of benzene. The biphenyl was added at the start of the experiment to give a concentration of 2% w/v.

cis-1,2-Dihydroxy-3-fluorocyclohexa-3,5-diene, cis-1,2-dihydroxy-3-phenylcyclohexa-3,5-diene and cis-1,2-dihydroxy-3-hydroxymethyl-cyclohexa-3,5-diene were obtained.

I claim:

1. A biologically pure culture of *Pseudomonas putida* NCIB 11767.

* * * * *